United States Patent [19]

Hlaban et al.

[11] 4,347,092
[45] Aug. 31, 1982

[54] PANTY LINER

[75] Inventors: James J. Hlaban, Neenah; Herbert E. Grube; Paul S. Woon, both of Appleton, all of Wis.

[73] Assignee: Kimberly-Clark Corporation, Neenah, Wis.

[21] Appl. No.: 153,210

[22] Filed: May 27, 1980

[51] Int. Cl.³ .............................................. B31F 23/10
[52] U.S. Cl. .................... 156/227; 128/284; 428/194; 156/291; 156/221
[58] Field of Search .................. 128/284, 287, 290 R, 128/290 W; 428/194; 156/314, 291, 221, 227, 200; 260/29.6 E

[56] References Cited

U.S. PATENT DOCUMENTS 1,969,636  8/1934  Alden ................................. 156/314
3,926,891 12/1975  Gross et al. .................... 260/29.6 E
4,176,667 12/1979  Herring ................................ 128/287

FOREIGN PATENT DOCUMENTS 623427  7/1961  Canada .......................... 128/290 W Primary Examiner—George F. Lesmes
Assistant Examiner—B. K. Johnson
Attorney, Agent, or Firm—Howard Olevsky; William D. Herrick

[57] ABSTRACT

A process is provided for making a panty liner type of feminine napkin having an absorbent pad and a fluid permeable cover which is coterminous with the absorbent pad at each of the longitudinal ends. The process involves adhering the wrap to the pad with a water-based emulsion adhesive, selectively moistening the pad and compressing the coterminous longitudinal ends.

1 Claim, 1 Drawing Figure

PANTY LINER

FIELD OF THE INVENTION

This invention relates to a sanitary napkin and particularly to a panty liner.

BACKGROUND OF THE INVENTION

Recently a new type of feminine napkin has attained substantial commercial success. This particular type of feminine napkin known as a panty liner is of limited capacity and is designed for use with intermenstrual vaginal discharge or, at other times when low levels of menstrual discharge occur.

Feminine napkins of the panty liner type, because they are designed to retain only minimal amounts of fluid, are smaller and more compact than the larger more absorbent conventional sanitary napkins.

Napkins of this type are designed to be flexible and soft. Flexibility is necessary so that the panty liner conforms to the perineal configuration, particularly as the wearer moves. Flexibility is important particularly at the peripheral edges because of the possibility of chafing which may result from the roughened edges contacting the tender skin in the perineal area.

One panty liner currently available provides for softness along its longitudinal sides by folding over the outer wrap and the absorbent to provide a soft edge along the sides of the napkin. This can be accomplished without particular difficulty along the sides, but not at the longitudinal ends. These ends feature coterminous layers of the wrap and absorbent pad which may chafe. The layers also may separate which not only increases chafing by exposing a plurality of ends to delicate tissue but also tend to destroy the integrity of the napkin and, even with the low levels of flow contemplated for use of the napkin could provide areas of leakage.

Attempts to eliminate the delamination at the ends of the panty liner type of product have been directed into two general areas. The first involes the use of compression or embossing of the layers at the ends. The second approach is to apply adhesive to the ends to adhere the wrap to the absorbent pad in the area. Both of these solutions have produced problems. While the adhesive does effectively prevent delamination it also stiffens the end portions eliminating the flexibility desired and decreasing the ability to maintain position during movement of the wearer. Contrarily, when embossing only is used, softness is maintained but when the ends are wet, delamination frequently occurs. Delamination, in fact, even occurs in the dry state after some period of use due to the motion applied to the ends during movement of the wearer. The disadvantages of both of these approaches have been overcome by the subject invention.

SUMMARY OF THE INVENTION

According to this invention, a process is provided which combines the use of a water-based emulsion adhesive with compression such as embossing to provide delamination resistant ends while maintaining the flexibility desirable in these regions. This is accomplished by moistening the pads at the longitudinal ends prior to compression.

Simply stated, this invention involves the steps of adhesively securing a fluid permeable outer wrap to an absorbent pad with the water-based emulsion adhesive. After the adhesion is complete, and the panty liner is assembled so that the outer wrap and absorbent pad are coterminous at the longitudinal ends, the ends are subjected to a moisture treatment, e.g. by spraying. This moisture treatment accomplishes two things. First, it tends to reactivate the adhesive, making it more responsive to the subsequent compression step and, secondly, due to the interaction of moisture and the cellulosic fibers present in the absorbent, after the compression step is completed, the ends remain relatively flexible.

After moisture treatment, the ends of the nakin are subjected to a compression step, e.g. by compression rolls or embossing rolls. This further activates the adhesive but, as mentioned before, due to the previous moistening of the absorbent in the area of the compression at the ends of the napkin, the napkin remains relatively flexible. The combination of compression and adhesion serves to almost completely eliminate problems associated with delamination.

BRIEF DESCRIPTION OF THE DRAWING

A particularly preferred embodiment of this invention can be seen from FIG. 1 which is a perspective view partially in cross section of a panty liner made in accordance with this invention.

DETAILED DESCRIPTION OF THE INVENTION

Figure 1:
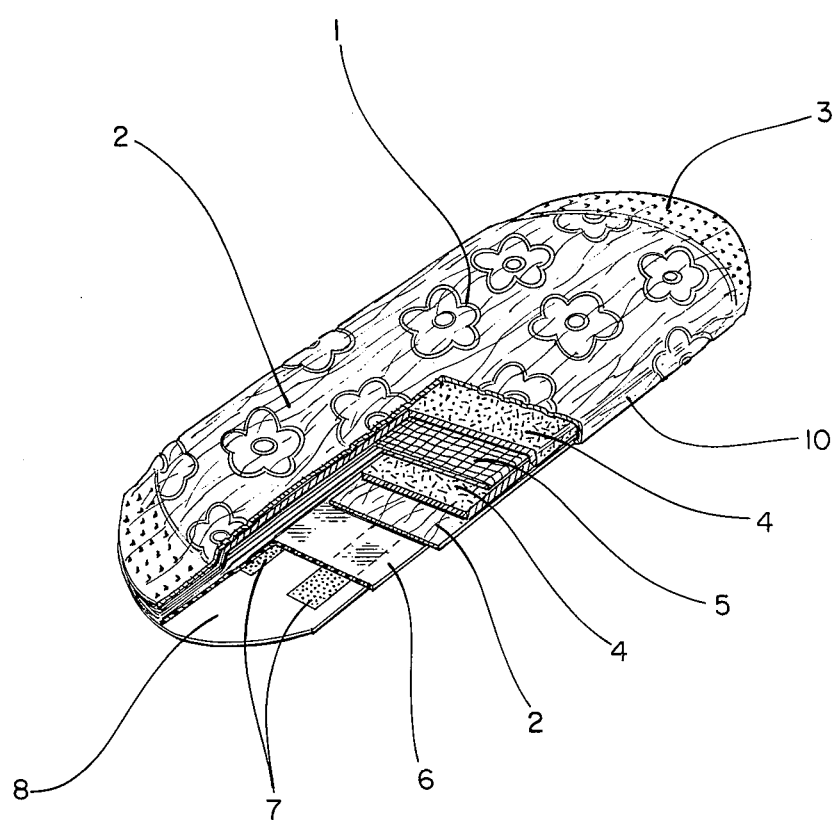

In this particular embodiment, the pad is assembled by air laying wood pulp fluff 4 on a carrier layer of scrim 5. A thin layer of water-based emulsion adhesive is then coated on the upper portion of the fluff and a covering material such as a bonded carded web 2 having an embossed pattern 1 is overlaid on the adhesive coated fluff 4. The adhesive is then coated on the scrim support and permeates it to attach it to the fluff 4. The adhesive also provides integrity to the fluff layer 4 and bonds it to the cover material 2.

At this point it is generally preferable to reduce the moisture content of the adhesive to aid in securing the individual layers. At this point in the process, all of the layers are coterminous around its entire periphery and is produced in long rolls approximately twice the width of the finished pad.

The composite is then subjected to a water spray at the areas to be compressed and additional water-based emulsion adhesive is applied in the wet area 3. The structure is folded over along the sides so that the side peripheral edges abut each other. As can be seen from FIG. 1, this produces a configuration in which the outer layers, both top and bottom, are the cover material 2. Scrim support material 5 is folded over on itself as the innermost layer, and the fluff 4 is positioned between the cover 2 and the scrim support 5 on either side of the scrim. The fold is maintained by gentle compression and the soft folded edge 10 is produced. The water impermeable baffle 6 is then adhesively attached in the abutted area.

Afterward the roll is embossed at each end to form the crimped end 3. Garment adhesive 7 and release paper 8 are then applied by conventional means and the ends formed. The napkin is then cut.

In order to practice the process of this invention and produce a panty liner with flexible ends resistant to delamination it is necessary to wet the outer wrap prior to embossment with enough water to moisten all of the layers of the composite in the area to be embossed. It is undesirable to saturate the ends because absorbency and flexibility would be diminished. As long as the absorbent is moist, sufficient water is used for the purpose of this invention.

While the invention in its broad concept relates to the panty liner with coterminous ends, the same type of adhesion water activation and compression can be accomplished around the entire periphery of the napkin with the same attendant benefits. If, contrarily, the type of napkin is used which employs the folded wrap and absorbent the combination of compression adhesion and moisture addition is not needed at the sides of the napkin.

What is claimed is:

1. A process for eliminating the delamination of the ends of a sanitary napkin having a fluid impervious baffle, an absorbent pad and a fluid permeable wrap said absorbent pad and said cover being coterminous and adhesively attached by a water soluble adhesive comprising:
   (a) folding said wrap and said pad along its longitudinal axis to produce a double thickness of said absorbent pad with said wrap surrounding said folded pad and the longitudinal edges of the wrapped pad being closely adjacent each other;
   (b) attaching said baffle to said wrapped pad over said longitudinal edge, said baffle being coterminous with said folded wrapped pad so that each end of the napkin has a coterminous folded layer of said absorbent pad and wrap and the end of said baffle;
   (c) moistening each of said ends;
   (d) applying a water based emulsion adhesive to said ends;
   (e) subjecting said ends to compressive force.

* * * * *